US012599350B2

(12) United States Patent
Naghavi

(10) Patent No.: US 12,599,350 B2
(45) Date of Patent: Apr. 14, 2026

(54) COMPUTED TOMOGRAPHY BASED IMAGING OF VASA VASORUM DENSITY FOR DETECTION AND MONITORING OF INFLAMMATION AND ANGIOGENESIS IN VASCULAR WALL

(71) Applicant: Morteza Naghavi, Long Beach, CA (US)

(72) Inventor: Morteza Naghavi, Long Beach, CA (US)

( * ) Notice: Subject to any disclaimer, the term of this patent is extended or adjusted under 35 U.S.C. 154(b) by 308 days.

(21) Appl. No.: 18/469,384

(22) Filed: Sep. 18, 2023

(65) Prior Publication Data

US 2024/0115224 A1       Apr. 11, 2024

Related U.S. Application Data

(60) Provisional application No. 63/414,561, filed on Oct. 9, 2022.

(51) Int. Cl.
*A61B 6/50* (2024.01)
*A61B 6/00* (2006.01)
*A61B 8/08* (2006.01)
*G06T 7/00* (2017.01)

(52) U.S. Cl.
CPC .............. *A61B 6/504* (2013.01); *A61B 6/481* (2013.01); *G06T 7/0012* (2013.01); *G06T 2207/10081* (2013.01); *G06T 2207/30101* (2013.01)

(58) Field of Classification Search
CPC ....... A61B 6/504; A61B 6/481; A61B 6/4417; A61B 8/12; A61B 6/503; A61B 6/5217; A61B 8/0883; A61B 8/0891; A61B 8/4416; A61B 6/032; G06T 7/0012; G06T 2207/10081; G06T 2207/30101
See application file for complete search history.

(56) References Cited

U.S. PATENT DOCUMENTS

| | | | |
|---|---|---|---|
| 10,695,023 B2 † | 6/2020 | Antoniades | |
| 11,383,137 B2 † | 7/2022 | Antoniades | |
| 11,779,292 B2 * | 10/2023 | Min | A61B 6/5205 600/300 |

(Continued)

OTHER PUBLICATIONS

Evangelos K. Oikonomou et al., A novel machine learning-derived radiotrasncriptomic signature of perivascular fat improves cardiac risk prediction using coronary CT angiography, pp. 1-15, 2019, Oxford. University Press, Oxford, UK.†

*Primary Examiner* — Siamak Harandi
(74) *Attorney, Agent, or Firm* — Pham Law PLLC; Frank Pham, Esq.

(57) ABSTRACT

According to an aspect of the present invention, there is provided a method for imaging vasa vasorum density of a vessel in the body such as coronary and carotid arteries and the aorta and thereby assessing the risk of adverse health outcomes for a patient, comprising administering a contrast agent to the patient; performing a contrast-enhanced CT scan to measure Hounsfield distribution and heterogeneity related to vasa vasorum density in and around the vessel wall of a patient; analyzing the data to determine a metric related to the density of the vasa vasorum; and recommending a diagnostic and/or therapeutic next step to the patient to prevent adverse health outcomes based at least in part on the metric related to the vasa vasorum density.

17 Claims, 6 Drawing Sheets

(56)             References Cited

U.S. PATENT DOCUMENTS

| 11,861,833 | B2 * | 1/2024 | Min | A61B 6/481 |
| 2010/0197580 | A1 * | 8/2010 | Tsopanoglou | A61P 27/02 |
| | | | | 514/6.9 |
| 2011/0319762 | A1 * | 12/2011 | Lerman | A61B 8/12 |
| | | | | 600/443 |
| 2022/0067933 | A1 * | 3/2022 | Alizad | G06T 7/73 |

* cited by examiner
† cited by third party

Figure 6:
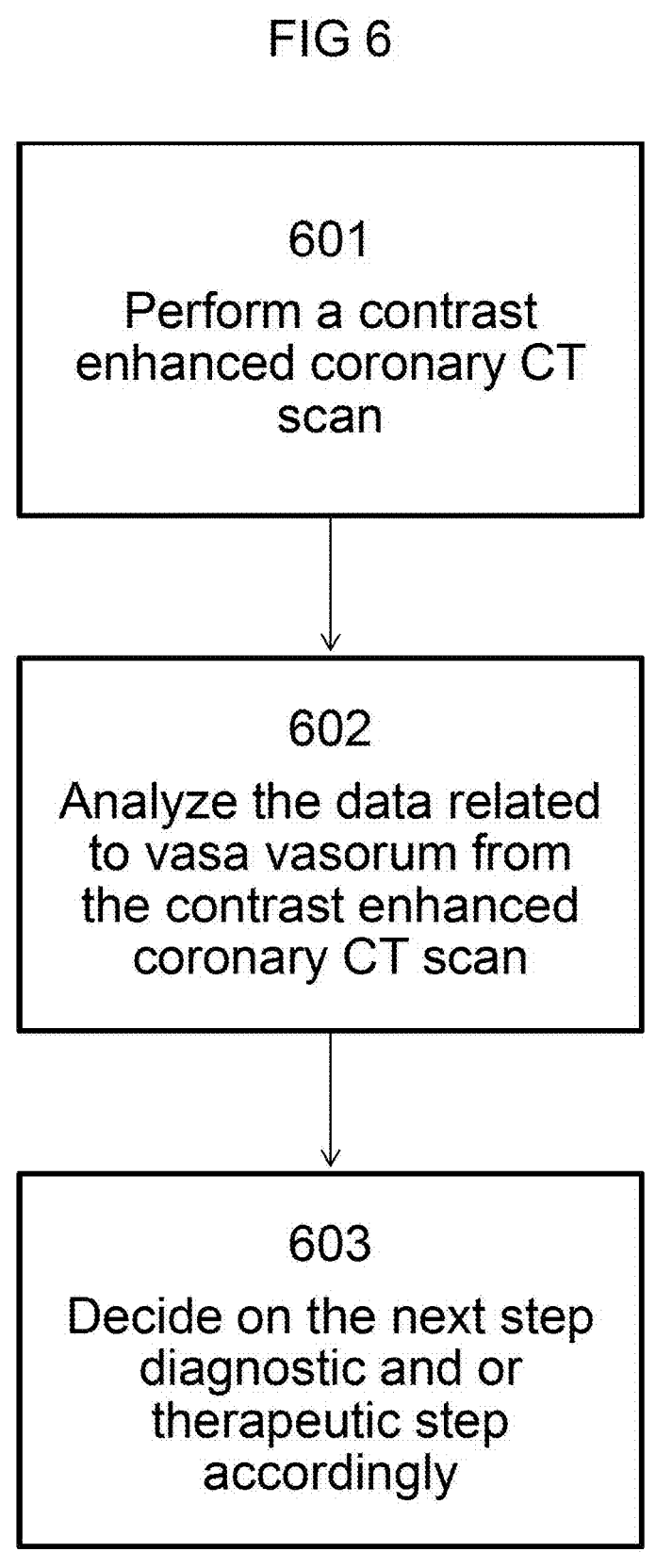

Perform a contrast enhanced coronary CT scan

602

Analyze the data related to vasa vasorum from the contrast enhanced coronary CT scan

603

Decide on the next step diagnostic and or therapeutic step accordingly

COMPUTED TOMOGRAPHY BASED IMAGING OF VASA VASORUM DENSITY FOR DETECTION AND MONITORING OF INFLAMMATION AND ANGIOGENESIS IN VASCULAR WALL

CROSS-REFERENCE

This application claims priority to U.S. Provisional Patent Application 63/414,561, filed Oct. 9, 2022.

BACKGROUND

Atherosclerosis is a chronic inflammatory disease of the arteries that is characterized by the formation of plaques on the inner walls of the arteries. These plaques can narrow or block the arteries, reducing blood flow to the heart, brain, and other organs. Atherosclerosis is the underlying cause of most heart attacks and strokes.

In the field of atherosclerotic plaque pathology, it has been known that proliferation of the vasa vasorum, the microvessels that supply oxygen and nutrients to the arterial wall, is associated with atherosclerosis and its complications. Atherosclerosis is very common and starts early in life. However, its complications, including heart attacks and strokes, which are the leading causes of death worldwide, occur later in life when atherosclerotic plaques become vulnerable to atherothrombotic events.

Vulnerable atherosclerotic plaques are plaques that are more likely to rupture and or cause a blood clot. These plaques are typically characterized by a large amount of lipids (fats) and a thin fibrous cap. When a plaque ruptures, it can trigger the formation of a blood clot, which can block the artery and lead to a heart attack or stroke. For this to occur clinically, and to result in fatal outcomes, usually other factors including blood thrombogenesity and myocardia vulnerability to arrythmia are required.

Inflammation (which is a broadly defined word to represent the reaction of body's immune system to defend against unexpected stimuli) plays a key role not only in the development of atherosclerosis but also in its complications. An active inflammation site is like an active battleground where immune cells constantly attack the unknown agents with cellular and humoral pathways. To maintain and succeed in this fight, the immune cells require constant delivery of blood that carries oxygen and nutrients. Almost always new blood vessels are needed much like new roads are needed to deliver foods and ammunition to a battlefront, such roads are microvessels and such a phenomenon is called angiogenesis, and such angiogenesis in and around the arteries become an extension of the vasa vasorum network which are microvessels feeding the vessel walls. These newly formed vessels are often lose and leaky hence can lead to extravasation of contrast agents inside an atherosclerosis plaque which is sometimes referred to as a "blush sign" in an X-ray image after injection of the an X-ray dye. Active immune cells like macrophages are like massive bodybuilders that engulf foreign bodies and oxidized lipid molecules hence need much more fuel than ordinary cells in the arterial wall hence the need for more blood supply and more vasa vasorum. Imaging these excess microvessels and their blood circulation using X-ray dye mixed blood under CT scans is the focus on this invention.

While it has been long perceived that imaging inflammation can be a useful metric in evaluating the risk of atherosclerosis, it has been difficult to assess using non-invasive means. Recent reports by investigators who claim imaging periadventitial fat is a reliable way of imaging coronary inflammation meets the skepticism of experts. The investigators insist that their technique is able to measure lipolysis by measuring reduction of fat signals around atherosclerotic plaques. This invention takes a contrary view and focused on measuring the increased Hounsfield density in and around the atherosclerotic plaques and coronary wall due to increase density of vasa vasorum and resulting HU enhancement by X-ray contrast agents (X-ray dye). Numerous pathology and CT imaging studies have clearly demonstrated increased fat around coronary arteries including epicardial and pericardial fat is associated with poor outcomes. Therefore, the notion of fat reduction contrasts such a large body of evidence. Contrary to fat attenuation hypothesis, the vasa vasrom density approach is in line with the common understanding of what goes on in body's sites of inflammation. Therefore, this invention can not only be used for imaging inflammation in and around coronary arterial walls but also in and around any vascular wall anywhere in the body that is permissible to contrast-enhanced CT based imaging.

Therefore, practical imaging systems for detection of increased vasa vasorum density and monitoring changes in vasa vasorum density are urgently needed.

SUMMARY OF INVENTION

The present invention provides methods and systems for measuring vasa vasorum density in and around the arteries in particular coronary arteries. The ultimate solution behind these techniques is to detect who is more likely to have a heart attack or stroke and to intervene in their trajectory by administering a treatment. The main imaging tool utilized in embodiments is a contrast enhanced coronary CT scan.

According to an aspect of the present invention, there is provided a method for assessing the cardiovascular disease risk of a patient, comprising: administering a contrast agent to the patient; performing a contrast enhanced coronary CT scan to measure Hounsfield Unit (HU) heterogeneity related to vasa vasorum density in and around the coronary arteries of a patient; analyzing the data from the contrast enhanced coronary CT scan to determine a metric related to the density of the vasa vasorum in and around the coronary arteries of the patient; and administering a therapy to the patient to treat or prevent cardiovascular disease based at least in part on the metric related to the density of the vasa vasorum in and around the coronary arteries of the patient.

BRIEF DESCRIPTION OF THE DRAWINGS

FIG. 6 illustrates a flowchart of a method used in embodiments for evaluating risk and recommending the next diagnostic or therapeutic step based on the vasa vasorum density observed.

DETAILED DESCRIPTION

Detection of increased vasa vasorum during contrast-enhanced computed tomography (CT) imaging is indicative of coronary artery disease.

Hence the new invention utilizes contrast enhanced coronary CT scans to measure vasa vasorum density in and around the coronary arteries. The principle foundations of this approach is based on the well-established knowledge that inflammation in particular chronic inflammation such as atherosclerotic coronary artery disease and other forms of chronic vasculitis result in excess proliferation of vasa vasorum, the tiny vessels that feed the arteries. The more inflammation the more traffic of blood flow to the area which requires higher density of microvasculature.

In embodiments, a CT scan can be performed, with and without contrast agent, starting with non-contrast as the screening step, and using contrast-enhanced coronary angiography for a selected population, with interpretation of the results of both automated powered by artificial intelligence (AI).

Figure 1:
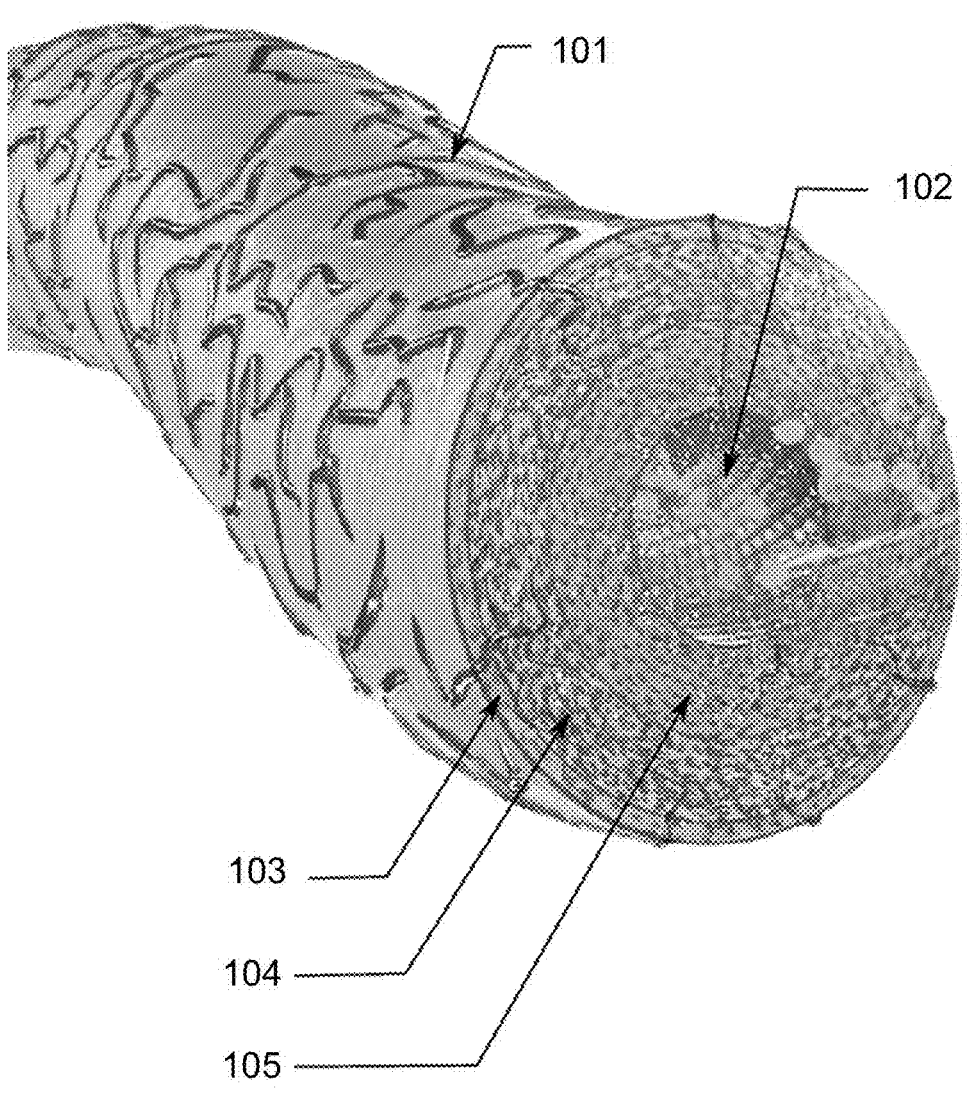
FIG. 1 illustrates the anatomy of an artery and the three layers of an arterial wall. Vasa vasorum are illustrated as tiny vessels surrounded and penetrating the arterial wall mostly from the outside (adventitial layer) but also from the inside (endothelial or luminal side).

FIG. 1 illustrates the anatomy of an artery and the three layers of an arterial wall. Vasa vasorum are illustrated as tiny vessels surrounded and penetrating the arterial wall mostly from the outside (adventitial layer) but also from the inside (endothelial or luminal side).

Vasa vasorum 101 are the vessels situated on the wall of the artery. Oxygenated blood flows through lumen 102 to supply nutrients and oxygen to cardiac muscle. Tunica adventitia 103 is the outer layer of the artery wall. Tunica media 104 is the middle layer of the artery wall. Tunica intima 105 is the inner layer of the artery wall.

Figure 2:
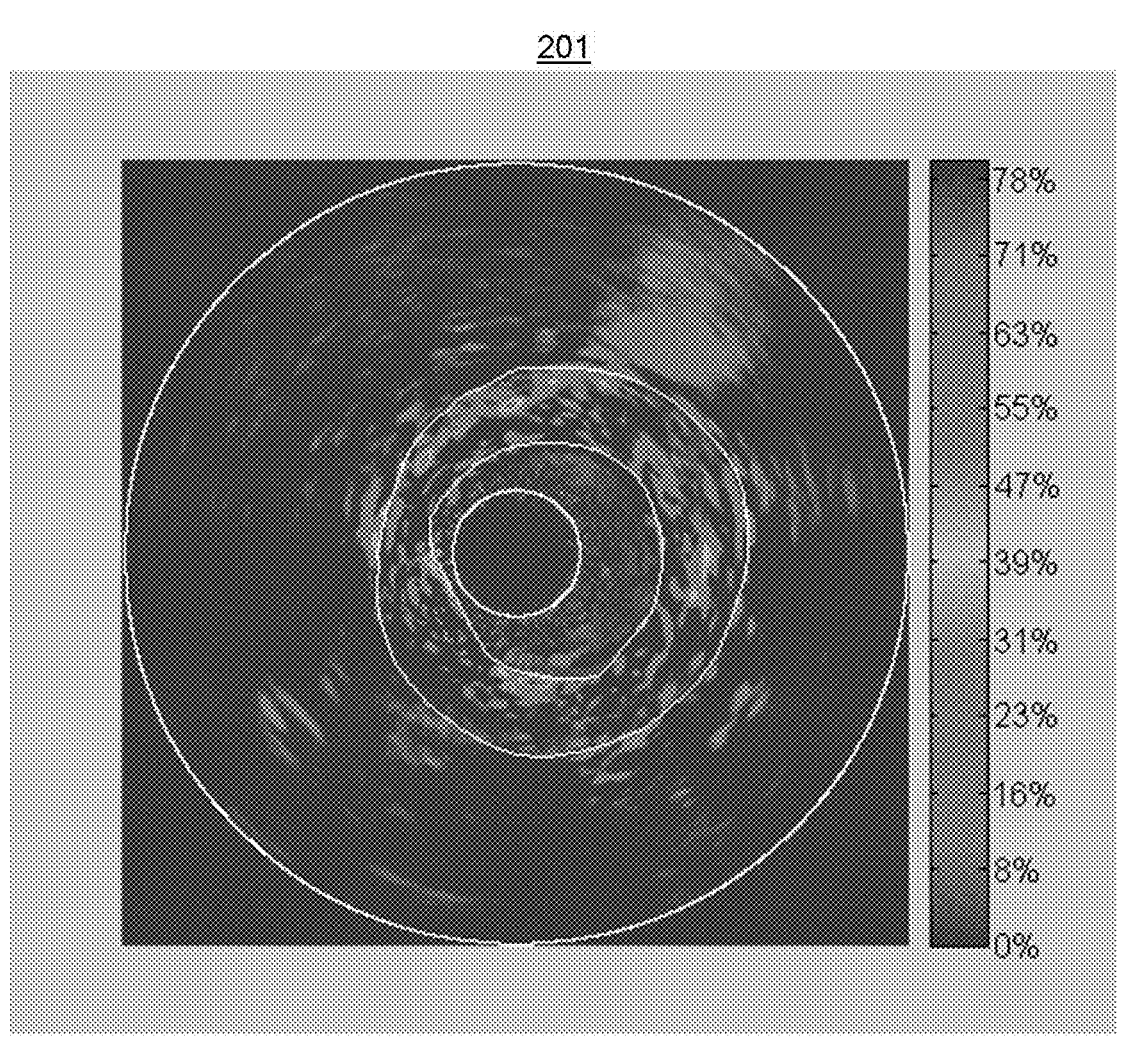
FIG. 2 illustrates prior art vasa vasorum imaging using microbubbles contrast-enhanced intravascular ultrasound (IVUS) subtraction analysis that only shows the microvessels containing microbubbles.

FIG. 2 illustrates prior art vasa vasorum imaging using microbubbles contrast-enhanced intravascular ultrasound (IVUS) subtraction analysis that only shows the microvessels containing microbubbles.

201 in FIG. 2 refers to prior art vasa vasorum imaging using microbubbles contrast-enhanced intravascular ultrasound (IVUS).

Coronary vasa vasorum imaging using microbubbles and intravascular ultrasound (IVUS) imaging devices is known. However, IVUS is a highly invasive procedure that requires a catheterization laboratory (like an OR) and penetrating patient's skin to access femoral or radial arteries and threading the IVUS catheter to the aorta and from the root of aorta into each of the major branches of coronary arteries. This is not only invasive but also expensive and ethically unjustifiable for most patients who could benefit from such information.

Figure 3:
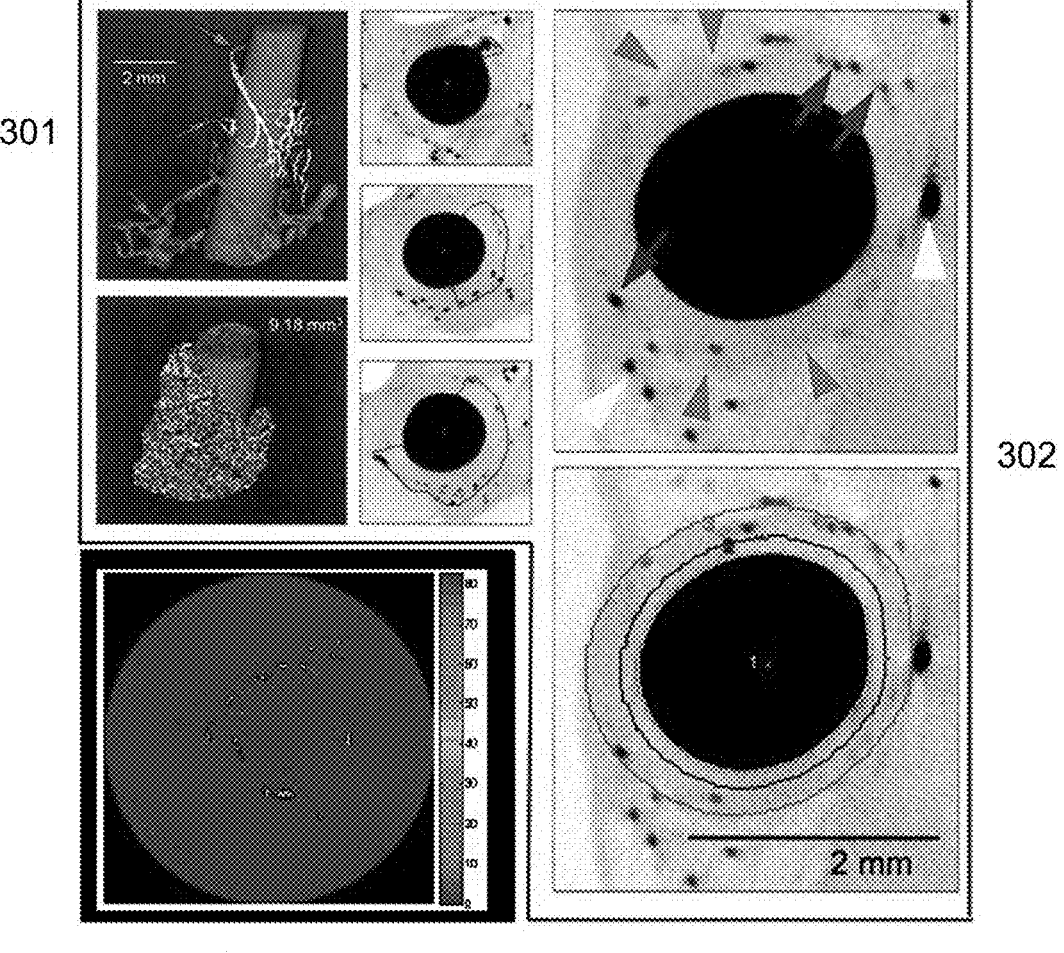
FIG. 3 illustrates vasa vasorum in contrast-enhanced intravascular ultrasound, contrast-enhanced microCT, and pathology slides.

FIG. 3 illustrates vasa vasorum in contrast-enhanced intravascular ultrasound, contrast-enhanced microCT, and pathology slides.

Contrast-enhanced microCT image 301 is obtained using Micro-CT. Micro-CT scanning is X-ray imaging in 3D, using the same method as medical CT (or "CAT") scans, but micro-CT is on a much smaller scale with greatly increased resolution. Pathology slides 302 have been prepared by a pathologist slicing the tissue block containing vasa vasorum into very thin layers that are placed on a glass slide and examined under a microscope. Contrast-enhanced intravascular ultrasound (IVUS) image 303 is a prior art image as described with reference to FIG. 2.

Figure 4:
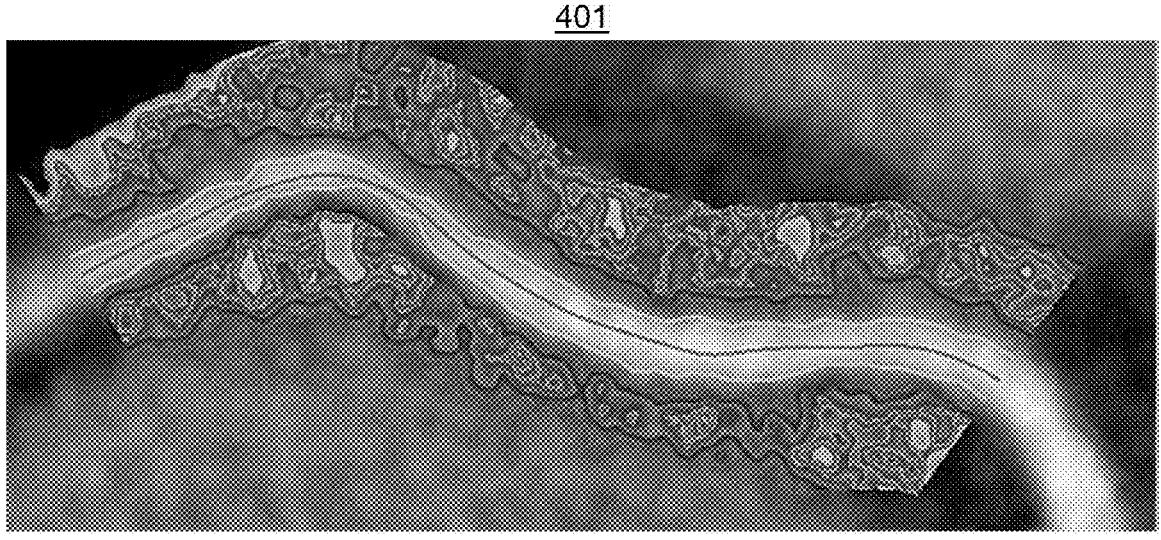
FIG. 4 illustrates a demonstration of peri-arterial (adventitial and periadventitial) Hounsfield Unit heterogeneity caused by the network of vasa vasorums and CT contrast agent (X-ray dye) circulating inside the vasa vasorum. High intensity sports resemble larger vasa vasorums with higher amounts of blood containing X-ray dye.

FIG. 4 illustrates a demonstration of peri-arterial (adventitial and periadventitial) Hounsfield Unit heterogeneity caused by the network of vasa vasorums and CT contrast agent (X-ray dye) circulating inside the vasa vasorum. High intensity sports resemble larger vasa vasorums with higher amounts of blood containing X-ray dye.

Image 401 in FIG. 4 illustrates a demonstration of Arterial Wall and Peri-Arterial Hounsfield unit heterogeneity caused by vasa vasorum density and CT contrast agent circulating inside the vasa vasorum.

It can be observed that there is heterogeneity in the attenuation around the coronary arteries depicted in FIG. 4, as measured in Hounsfield units (HU), where Hounsfield units are defined as the attenuation value of the X-ray beam in a given voxel, minus the attenuation of water, divided by the attenuation of water, multiplied by 1000.

The reason for heterogeneity in the HU density of the surrounding of the wall is the vasa vasorum surrounding the wall. The vasa vasorum is a network of vessels and as such has spaces between the vessels where attenuation is less. If the attenuation was being caused by adipose tissue, the heterogeneity observed would not be present. The HU density of the actual wall of the coronary arteries is also affected by changes in the density of VV.

The more inflammation, the higher the VV density, the more contrast agent circulating inside VV in & around the coronary walls, the higher the HU density in & around the coronary wall. In contrast, the more intensive treatment, the less inflammation, the less VV density, the less contrast agent circulating inside VV in & around the coronary walls, the less the HU density in & around the coronary wall.

The change is HU density around the coronary walls observed in a second CT performed without administering additional contrast agent some time after a first contrast CT of VV of a coronary artery proves that the vasa vasorum is causing the attenuation observed in the first contrast CT scan. The contrast agent circulates in the vessels of the VV, and as the concentration of the contrast agent declines (because the contrast agent is eliminated), the observed HU density decreases.

The alternative hypothesis that the HU density around the coronary walls observed on a contrast coronary CT is due to the density of fat around the walls is mistaken because the HU attenuation due to the density of fat would be the same on a second contrast CT taken after some time and without administration of additional contrast agent, and in fact HU attenuation declines on the repeat CT.

Figure 5:
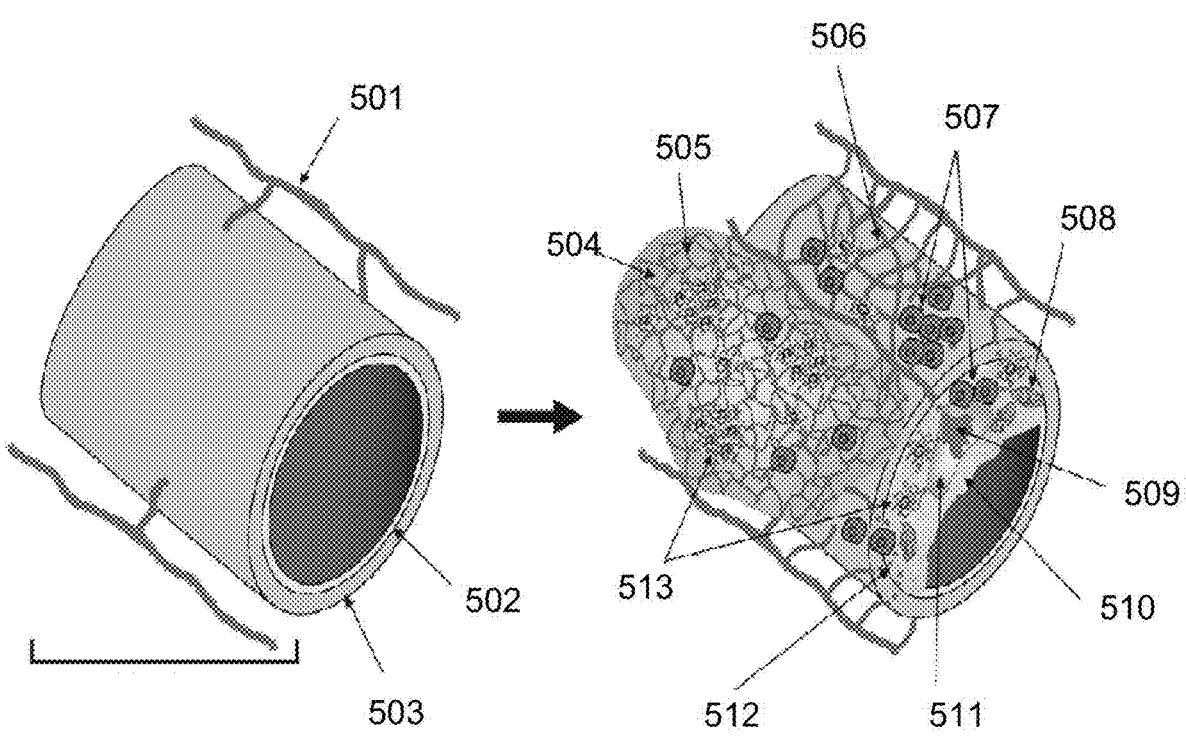
FIG. 5 illustrates normal vasa vasorum (low VV density) and vasa vasorum in an atherosclerotic arterial wall (high VV density).

FIG. 5 illustrates normal vasa vasorum (low VV density) and vasa vasorum in an atherosclerotic arterial wall (high VV density).

On the left of FIG. 5, vasa vasorum 501 services a normal artery with intima 502 and media 503. This is a normal artery without atherosclerosis present.

On the right of FIG. 5, proliferated vasa vasorum 506 serves an artery showing signs of atherosclerosis. Inflammatory cells 507 and smooth muscle cells 508 contribute towards a narrowing of the atherosclerotic artery. Intraplaque hemorrhage 509 is blood pooled in the artery wall. Athersclerotic plaque 510 narrows the artery wall and causes risks associated with cardiovascular disease. Necrotic core 511 is a hypocellular region containing remnants of dead cells. Invasion of vasa vasorum into the plaque 512 is the blood vessel network serving the plaque. Macrophages 513 are recruited to the necrotic core 511. Perivascular adipose tissue 504 is fat surrounding the artery. Capillaries in adipose tissue 505 are the blood vessels which service the perivascular adipose tissue.

FIG. 6 illustrates a flowchart of a method used in embodiments for evaluating risk and recommending the next diagnostic or therapeutic step based on the vasa vasorum density observed.

Step 601 is performing a contrast enhanced coronary CT scan to measure attenuation related to vasa vasorum density in and around the coronary arteries of a patient. For example, data could be gathered along a length of one or more of left main coronary artery, left anterior descending coronary artery, left circumflex coronary artery, and right coronary artery.

Step 602 is analyzing the data from the contrast enhanced coronary CT scan to determine a metric related to the density of the vasa vasorum in and around the coronary arteries of the patient. Analysis of the data could be done using artificial intelligence, for example, on a deep neural network trained with many images of vasa vasorum.

Step 603 is deciding whether and what therapy and/or a diagnostic test to administer to the patient to treat or prevent cardiovascular disease based at least in part on the metric related to the density of the vasa vasorum in and around the coronary arteries of the patient. Treatment for atherosclerosis may include lifestyle changes, medicine, and surgery, for example.

References regarding vasa vasorum and atherosclerosis include the following articles.

Yan A, Gotlieb A I. The microenvironment of the atheroma expresses phenotypes of plaque instability. Cardiovasc Pathol. 2023 Aug. 16; 67:107572. doi: 10.1016/j.carpath.2023.107572. Epub ahead of print. PMID: 37595697. https://pubmed.ncbi.nlm.nih.gov/37595697/

Chen D, Zhao Z, Liu P, Liu X, Wang X, Ren Q, Chang B. Adventitial Vasa Vasorum Neovascularization in Femoral Artery of Type 2 Diabetic Patients with Macroangiopathy Is Associated with Macrophages and Lymphocytes as well as the Occurrence of Cardiovascular Events. Thromb Haemost. 2023 Apr. 10. doi: 10.1055/s-0043-1768162. Epub ahead of print. PMID: 37037199. https://pubmed.ncbi.nlm.nih.gov/37037199/

Hillock-Watling C, Gotlieb A I. The pathobiology of perivascular adipose tissue (PVAT), the fourth layer of the blood vessel wall. Cardiovasc Pathol. 2022 November-December; 61:107459. doi: 10.1016/j.carpath.2022.107459. Epub 2022 Jul. 28. PMID: 35907442. https://pubmed.ncbi.nlm.nih.gov/35907442/

Guggenberger K V, Torre G D, Ludwig U, Vogel P, Weng A M, Vogt M L, Fröhlich M, Schmalzing M, Raithel E, Forman C, Urbach H, Meckel S, Bley T A. Vasa vasorum of proximal cerebral arteries after dural crossing—potential imaging confounder in diagnosing intracranial vasculitis in elderly subjects on black-blood MRI. Eur Radiol. 2022 February; 32(2):1276-1284. doi: 10.1007/s00330-021-08181-5. Epub 2021 Aug. 4. PMID: 34347156; PMCID: PMC8795054. https://pubmed.ncbi.nlm.nih.gov/34347156/

Li M, Qi Z, Zhang J, Zhu K, Wang Y. Effect and Mechanism of Si-Miao-Yong-An on Vasa Vasorum Remodeling in ApoE−/− Mice with Atherosclerosis Vulnerable Plague. Front Pharmacol. 2021 Apr. 14; 12:634611. doi: 10.3389/fphar.2021.634611. PMID: 33935723; PMCID: PMC8080061. https://pubmed.ncbi.nlm.nih.gov/33935723/

Ito H, Wakatsuki T, Yamaguchi K, Fukuda D, Kawabata Y, Matsuura T, Kusunose K, Ise T, Tobiume T, Yagi S, Yamada H, Soeki T, Tsuruo Y, Sata M. Atherosclerotic Coronary Plaque Is Associated With Adventitial Vasa Vasorum and Local Inflammation in Adjacent Epicardial Adipose Tissue in Fresh Cadavers. Circ J. 2020 Apr. 24; 84(5):769-775. doi: 10.1253/circj.CJ-19-0914. Epub 2020 Apr. 10. PMID: 32281556. https://pubmed.ncbi.nlm.nih.gov/32281556/

Cattaneo M, Sun J, Staub D, Xu D, Gallino J M, Santini P, Porretta A P, Yuan C, Balu N, Arnold M, Froio A, Limoni C, Wyttenbach R, Gallino A. Imaging of Carotid Plaque Neovascularization by Contrast-Enhanced Ultrasound and Dynamic Contrast-Enhanced Magnetic Resonance Imaging. Cerebrovasc Dis. 2019; 48(3-6):140-148. doi: 10.1159/000504042. Epub 2019 Oct. 29. PMID: 31661690. https://pubmed.ncbi.nlm.nih.gov/31661690/

Quan K, Song J, Yang Z, Wang D, An Q, Huang L, Liu P, Li P, Tian Y, Zhou L, Zhu W. Validation of Wall Enhancement as a New Imaging Biomarker of Unruptured Cerebral Aneurysm. Stroke. 2019 June; 50(6):1570-1573. doi: 10.1161/STROKEAHA.118.024195. Epub 2019 Apr. 30. PMID: 31035900. https://pubmed.ncbi.nlm.nih.gov/31035900/

Papaioannou T G, Vavuranakis M, Androulakis A, Lazaros G, Kakadiaris I, Vlaseros I, Naghavi M, Kallikazaros I, Stefanadis C. In-vivo imaging of carotid plaque neoangiogenesis with contrast-enhanced harmonic ultrasound. Int J Cardiol. 2009 May 29; 134(3):e110-2. doi: 10.1016/j.ijcard.2008.01.020. Epub 2008 May 20. PMID: 18495267. https://pubmed.ncbi.nlm.nih.gov/18495267/

Having thus described a few particular embodiments of the invention, various alterations, modifications, and improvements will readily occur to those skilled in the art. Such alterations, modifications, and improvements are intended to be part of this description though not expressly stated herein, and are intended to be within the spirit and scope of the invention. Accordingly, the foregoing description is by way of example only, and not limiting. None of the descriptions in the specification are intended to be imported into the claims, and nothing in the specification should be construed to limit any of the claims below.

What is claimed is:

1. A method for imaging inflammation based on quantifying vasa vasorum density in and around a coronary artery wall, comprising:

performing contrast-enhanced coronary computed tomography angiography (CCTA);

processing the acquired image data to measure the Hounsfield Units (HU) of voxels corresponding to contrast-enhanced microvascular structures representing vasa vasorum density within the coronary artery wall and the immediately adjacent adventitia;

reporting the quantified contrast-enhanced vasa vasorum density for the coronary arteries; and recommending a diagnostic or therapeutic course of action for the patient based on the measured vasa vasorum density, wherein a higher vasa vasorum density indicates a higher risk of adverse cardiovascular outcomes.

2. The method of claim 1 further comprising a step of using a computer enabled risk calculator, wherein the risk calculator is configured to evaluate the patient based at least in part on the coronary artery calcification data, coronary plaque composition data, coronary physiology data, electrocardiogram and other clinical and laboratory diagnostic data, patient's age and sex, medical history and relevant risk factors.

3. The method of claim 2, further comprising a step of preparing for optimizing coronary revascularization procedures based at least in part on the measured density of the vasa vasorum in and around the coronary arteries of the patient.

4. The method of claim 2, wherein the measured density is used to create color coded map along the length and cross-section of a coronary artery.

5. The method of claim 4, further comprising risk assessment in patients with genetic predisposition for excessive vascular formation and angiogenesis based at least in part on the measured density of the vasa vasorum in and around the arteries of the patient.

6. The method of claim 2, wherein the data gathered from the vasa vasorum density is used to facilitate drug development for treatment of coronary heart disease and associated complications.

7. The method of claim 2, wherein the data gathered from the vasa vasorum density is used to facilitate clinical trials for studying diagnostic or therapeutic approaches to manage coronary heart disease and associated complications.

8. The method of claim 2, wherein the data gathered from the vasa vasorum density is used to facilitate clinical trials for studying diagnostic or therapeutic approaches to manage cancer and associated complications.

9. The method of claim 1, further comprising a step of assessing vasa vasorum density within the wall and the immediately adjacent adventitia of aorta, carotid, iliac, femoral, and cerebral arteries.

10. The method of claim 1, wherein artificial intelligence is used to train for quantitative measurement of vasa vasorum density and monitoring changes in vasa vasorum density and to facilitate related analysis.

11. The method of claim 1, wherein the vasa vasorum density data from the computed tomography scan is gathered within the wall and along a length of one or more of aorta, carotid artery, femoral artery, cerebral arteries, as well as left main coronary artery, left anterior descending coronary artery, left circumflex coronary artery, and right coronary artery.

12. The method of claim 11, further comprising a step of predicting the risk of the patient experiencing a sudden death or a major adverse cardiovascular event based at least in part on the measured density of the vasa vasorum in and around the arteries of the patient.

13. The method of claim 1, further comprising a step of performing a dynamic subtraction analysis of contrast enhanced CT angiography images of a segment of ana artery to measure changes in Hounsfield Units related to vasa vasorum density in and around the segment of the artery of a patient.

14. The method of claim 13, further comprising the data obtained from late enhancement of the contrast enhanced coronary CT scan in and around the wall of the coronary artery indicating leaking vasa vasorum and extravasation of the contrast agent into the wall or surrounding the coronary arteries related to coronary "blush sign".

15. The method of claim 1, wherein the data gathered from the vasa vasorum density can improve risk assessment for patients with or at risk of aneurysms in aorta and other arteries.

16. The method of claim 1, wherein the data gathered from the vasa vasorum or angiogenesis density in and around the cancer tumors can improve risk assessment for cancer patients and monitoring angiogenesis inhibitors and other tumor suppressing agents that result in lowering the number of cancer cells therefore lowering the number of required micro-vessels to feed these cancer cells in a tumor.

17. The method of claim 1, wherein the CCTA is replaced with a virtual CCTA that results in a coronary segmentation without a contrast agent and the measured Hounsfield Units in and around the coronary wall reflects the density of blood inside the vasa vasorum.

* * * * *